United States Patent [19]

Burk et al.

[11] 3,994,157
[45] Nov. 30, 1976

[54] PELLET CRUSHING STRENGTH TESTER

[75] Inventors: James R. Burk; Robert C. Bates, both of Monroe, La.

[73] Assignee: Cities Service Company, Tulsa, Okla.

[22] Filed: July 21, 1975

[21] Appl. No.: 597,802

[52] U.S. Cl. .................................................. 73/94
[51] Int. Cl.² ......................................... G01N 3/16
[58] Field of Search ........................... 73/94, 161, 90

[56] References Cited

UNITED STATES PATENTS

| | | | |
|---|---|---|---|
| 2,930,943 | 3/1960 | Ruge | 73/161 X |
| 2,975,630 | 3/1961 | Michel | 73/94 X |
| 3,457,779 | 7/1969 | Hahn et al. | 73/94 |
| 3,610,034 | 12/1969 | Gunn et al. | 73/94 |

Primary Examiner—Jerry W. Myracle
Attorney, Agent, or Firm—Elton F. Gunn

[57] ABSTRACT

An apparatus and a method is disclosed for determining the crushing strength of pellets of a powdered material by compressing individual pellets between one pellet-contacting face on a force-exerting means and another pellet-contacting face on a force-measuring transducer. The transducer provides an output current at a voltage which varies in correspondence to the compressive force that is applied to a pellet during the crushing thereof. Accordingly, a pellet is first placed between the aforesaid pellet-contacting faces and the force exerting means is then driven toward the transducer at a controlled rate for compression and crushing of the pellet. Current voltage from the transducer is recorded permanently on a chart or else temporarily by means of a peak voltage remembering module in conjunction with a voltmeter having a digital read-out.

20 Claims, 7 Drawing Figures

PELLET CRUSHING STRENGTH TESTER

BACKGROUND OF THE INVENTION

Many materials produced in the form of a light, fluffy powder are pelletized prior to shipping in order to increase the bulk density of the material and improve the conveying and handling thereof. Examples of such materials include pigment grade silicas and carbon blacks which can be used, for example, as reinforcing agents for rubber, coloring or thickening agents for paints or inks, fillers for plastics, etc. Even though the pellets of such materials must necessarily have sufficient strength to withstand pulverization during the bulk shipment, conveying and handling thereof, it will nonetheless be appreciated that the pellets cannot be too resistive to a milling or grinding operation which is carried out for the purpose of redispersing the powder particles in the pellets so that they can be uniformly distributed within the medium in which they are to be used, e.g. a rubber, a paint vehicle, a plastic, etc. It is thus important that a test be available whereby the crushing strength of a pelleted material can be reliably determined in order to assure that produced pellets are strong enough to resist shipping and handling in bulk, but not so strong as to resist redispersion of the contained powder particles when the material is being distributed in such a medium.

One device for testing the crushing strength of pellets is disclosed in U.S. Pat. No. 3,331,241. In accordance with the description therein, pellets are glued to an elongated strand of tape at intervals, and the tape is then pulled through a gap between a force-measuring transducer and the end of a thrust-exerting rod which is continuously urged toward the foot of the transducer by means of a tensioned spring. The transducer delivers an output current at a voltage that varies in correspondence to the compressive force applied to the pellet for the purpose of crushing it. This voltage is measured with a voltmeter. A pellet, while attached to the tape, is thus dragged into a tapered gap between the force-exerting means and the foot of the transducer, and since this gap is smaller than the diameter of the pellet and since the forcing exerting means is continuously urged toward the foot of the transducer, the pellet is eventually crushed before it is pulled all the way through the gap.

Several disadvantages are associated with a pellet crushing strength tester of the type just described:

1. The resiliency of both the glue and the tape beneath each pellet can vary, hence interferring with accurate determination of the force actually required for crushing each pellet.

2. By pulling the tape into the tapered gap between the force-exerting means and the foot of the transducer, these members tend to be forced apart since the gap spacing is smaller than the diameter of the pellets, and this results in forces being exerted laterally against the pellet compression members. These laterally exerted forces detract from accurate determination of crushing strength since such forces can vary with differences in tape speed and the size and shape of the pellets.

3. In order to minimize error in measuring the crushing force, the tape and the glue for attaching the pellets thereto must be specially made up from carefully selected materials. In addition, a tedious procedure of attaching the pellets to the tape at spaced intervals must be followed, and still a second strand of tape must be used on the other side of the pellets to shield the working surfaces of the force-exerting means and the foot of the transducer from an accumulation of glue and powder.

4. The gap spacing between the force-exerting means and the foot of the transducer is critical in that it must be small enough to assure crushing of each pellet and yet large enough to assure transporting of pellets all the way through the gap by means of the tape.

It is therefore a principle object of the present invention to overcome the aforesaid disadvantages in a pellet crushing strength tester in order to simplify the testing procedure while obtaining reliable crushing strength test values. This and other objects and advantages of the invention will become apparent from the following description and the appended claims.

SUMMARY OF THE INVENTION

The present invention resides in apparatus for determining strength of pellets wherein individual pellets are crushed between a force-exerting means and a force-measuring transducer which supplies an output current having a voltage that varies in correspondence to changes in compressive force being exerted on a pellet being crushed. The force-exerting means has a pellet-contacting face which opposes another pellet-contacting face on the force measuring transducer, and means are also included for determining voltage generated by the transducer.

In accordance with the present invention, means are provided whereby the aforesaid pellet-contacting faces are first maintained apart from each other at a minimum distance which is greater than the diameter of a pellet to be tested. Subsequently, a driving means moves one of the pellet-contacting faces toward the other face until the minimum distance therebetween is at least as small as a pellet to be crushed. Movement of one of the pellet-contacting faces toward the other face can be accomplished by movement of either the force-exerting means toward the transducer, vice versa, or by movement of both toward each other. Advantageously, the transducer can be stationarily mounted whereas the force exerting means remains movable by the driving means.

In accordance with specific embodiments of the present invention, the force-exerting means comprises a special thrust assembly and driven means are provided for applying force to the pellet at a controlled, uniform rate until it is crushed. More specifically, the thrust assembly can have a stationarily mounted guide means with a thrust rod that is slidable back and forth therein. Advantageously, the thrust rod is non-rotatable in the bushing, and has a pellet-contacting face on one end which opposes a pellet-contacting face on the foot of the transducer. When a pellet is to be crushed, it is first placed between the aforesaid pellet contacting faces, and the driven, force-applying means then pushes the thrust rod toward the foot of the transducer, at a controlled, uniform rate, and this pushing of the rod is continued until the pellet is crushed.

When determining the crushing strength of a pellet by means of the apparatus just described, the opposing faces of the thrust rod and the transducer foot are first spaced apart at a distance significantly greater than the diameter of the pellet. The pellet is then placed between the opposed faces and the thrust rod is then driven toward the foot of the transducer at a controlled rate until the pellet is crushed. The voltage output of the transducer can be monitored during compression of the pellet, and is recorded at the time the pellet is crushed. Advantageously, the axis along which the thrust rod is driven is coaxial with that along which a thrust shaft of the transducer moves for generation of an electric output therefrom.

DESCRIPTION OF PREFERRED AND ALTERNATIVE EMBODIMENTS

Figure 1:
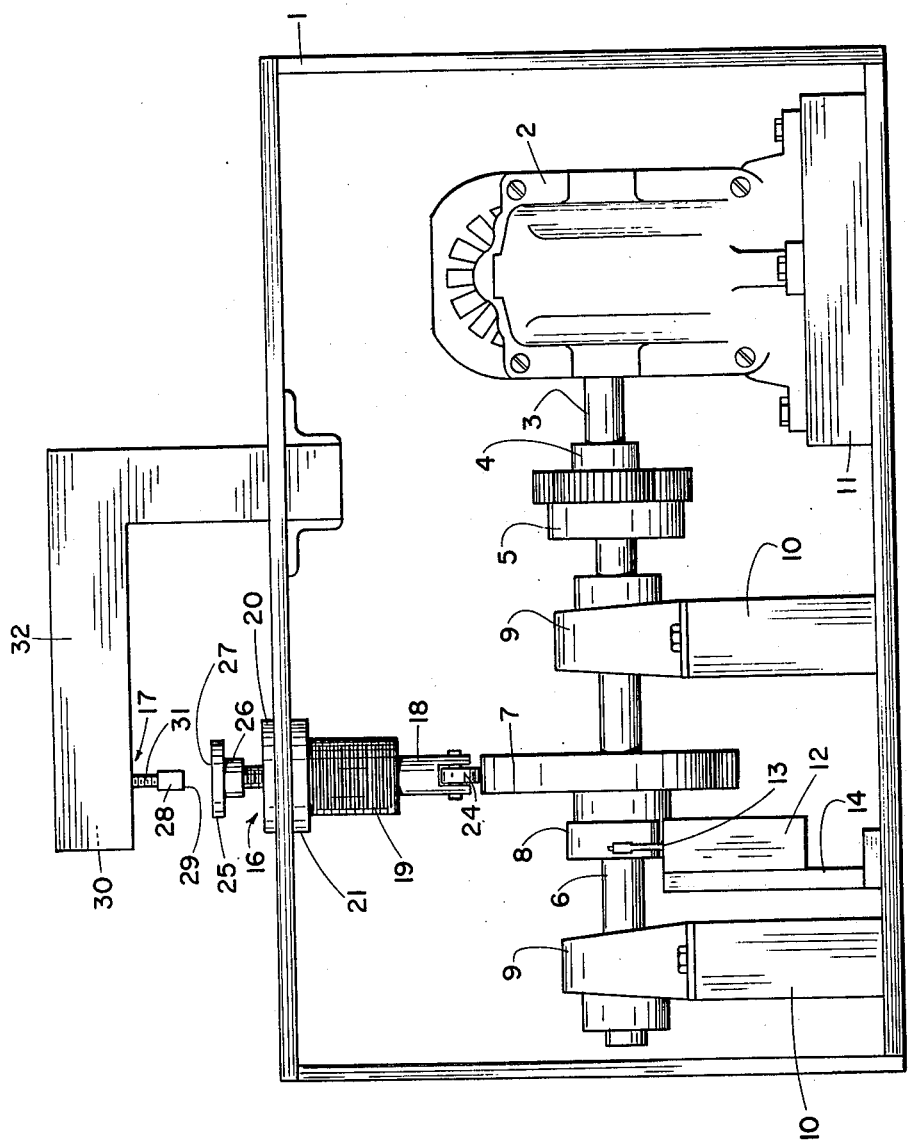
FIG. 1 is a side view of a pellet crushing apparatus constructed in accordance with the present invention.
Figure 2:
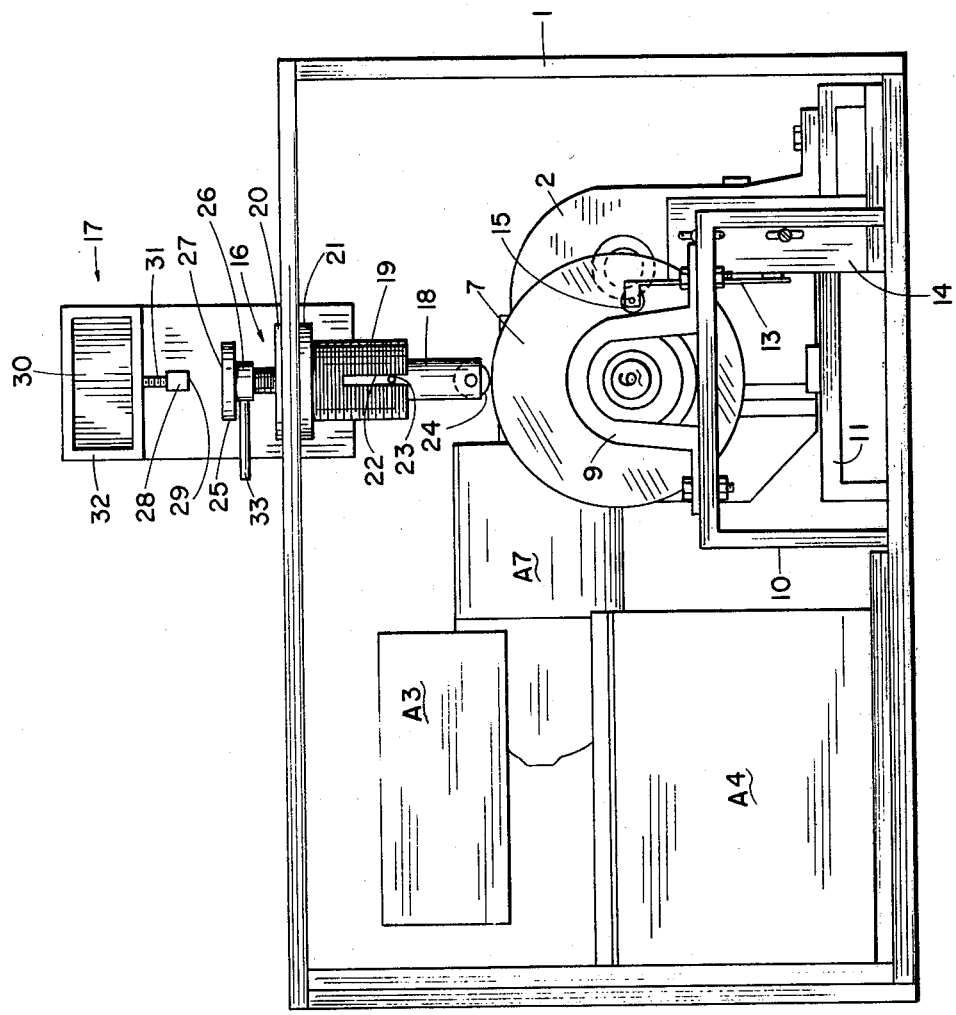
FIG. 2 is a front view of the apparatus of FIG. 1.
Figure 3:
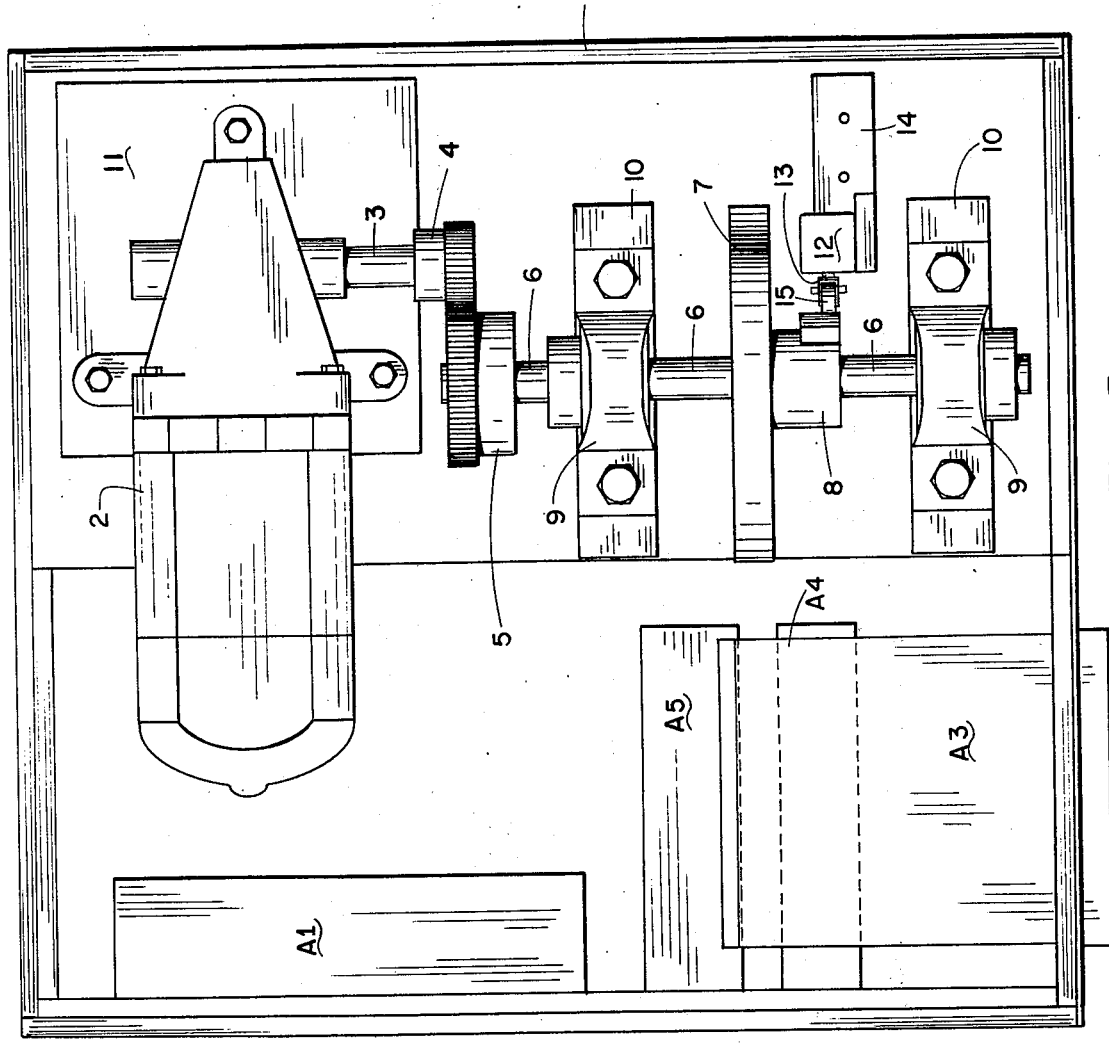
FIG. 3 is a top view of the apparatus of FIGS. 1 and 2.

Referring to FIGS. 1–3, a cabinet 1 encloses a gearmotor 2 having a driveshaft 3 and an attached gear 4 which meshes with a larger gear 5 on shaft 6. A primary cam 7 and a secondary cam 8 are also mounted on shaft 6, and the shaft is supported and stabilized from the ends by means of pillow block bearings 9 which are attached to bearing mounts 10. In similar fashion, the gearmotor 2 is supported and stabilized by mount 11. Microswitch 12, having an actuator lever 13, is attached to a mount 14 therefor. A wheel 15 on the switch actuator lever 13 rides on secondary cam 8 thus actuating the switch 12 and thereby changing the speed of the gearmotor from a high to a low speed, and vice versa, upon rotation of the cam.

Figure 6:
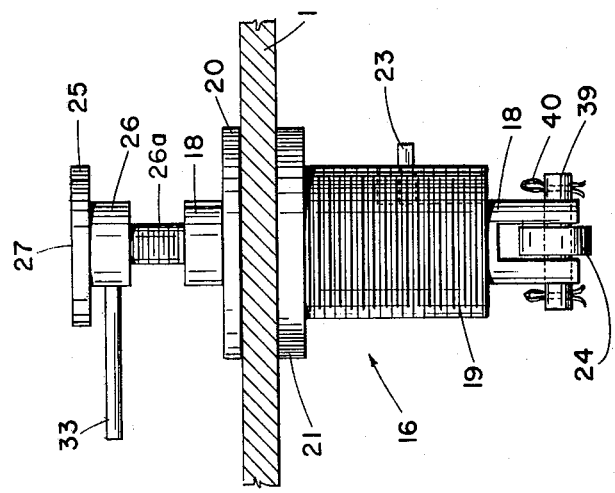
FIG. 6 represents a thrust assembly which can be used as a force-exerting means with the apparatus shown in FIGS. 1–5.

The thrust assembly for exerting compressive force on pellets to be crushed is generally represented at 16, whereas the force-measuring transducer, e.g. a load cell, is generally indicated at 17. As shown in FIGS. 1 and 6, the thrust assembly comprises a thrust rod 18 which passes through a bushing 19. The bushing has a shoulder 20 at the top end and a threaded nut 21 beneath it which screws onto the bushing. By means of shoulder 20 and nut 21, the bushing is securely fastened in a hole therefor in the top of cabinet 1. The upper end of rod 18 extends outside of the cabinet whereas the lower end projects downward toward cam 7.

Thrust rod 18 is slidable in bushing 19 but is not rotatable therein. Non-rotation of the rod is assured by use of a keyway 22 in the wall of the bushing and key 23 which is attached to the rod and fits in the keyway.

A wheel 24 is attached to the lower end of the rod 18 and provides a rolling surface for contact with cam 7. Since the rod 18 moves freely back and forth within the bushing, it is pushed upward by the eccentric portion of cam 7 upon upward rotation thereof and drifts downward by gravity when the eccentric of the cam rotates to a downward position. A pellet-receiving plate 25 is attached to the upper end of rod 18 by means of female threads in the base 26 of the plate and matching male threads on the rod. The plate 25 has a pellet-contacting face 27 on the top side thereof, and this face is moved upward toward the foot 28 of transducer 17 when rod 18 is thrust upward by cam 7. Foot 28 also has a pellet-contacting face 29, so that a pellet being crushed by the machine is confined between both of the faces 27 and 29.

As shown in the drawings, the foot 28 is below the main body 30 of the transducer 17 and is connected thereto by means of a thrust shaft 31. Transduction of mechanical force to electric current is accomplished in the main body 30 of the transducer when the foot 28 is urged upward by the pressing of a pellet against the face 29 of the foot upon upward movement of rod 18. The main body 30 of the transducer is stationarily mounted in a housing 32 therefor which is rigidly attached to cabinet 1.

A pellet receiving plate 25 having a base 26 and a male-threaded lower portion 26a is attached to the upper end of rod 18 by means of female threads thereon. For changing the distance between pellet-contacting faces 27 and 29, the plate 25 is turned by means of lever 33 so that it travels over the aforesaid threads and thus moves upward or downward depending upon the direction in which it is rotated.

Figure 5:
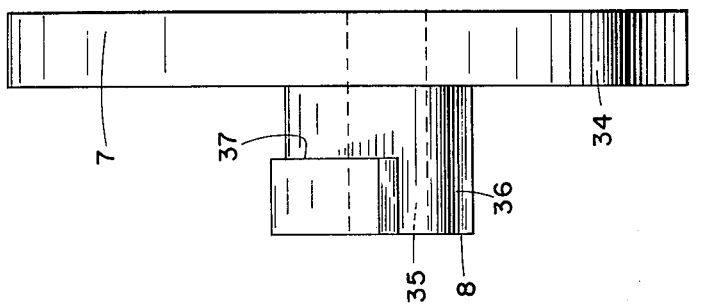
FIG. 5 is a side view of the cam shown in FIG. 4.
Figure 4:
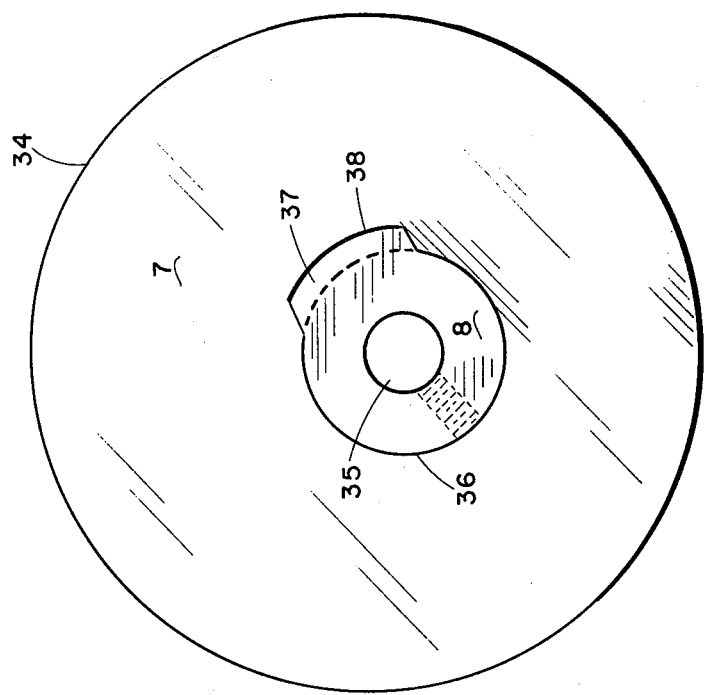
FIG. 4 is a front view of a cam which can be used with the apparatus of FIGS. 1–3.

Referring now to FIGS. 4 and 5, it can be seen that the primary and the secondary cams are integral. Alternatively, they can be made separately and mounted to shaft 6 independently of each other. The camming face 34 of cam 7 is circular but is off center with respect to central opening 35. Therefore, as shown in FIGS. 4 and 5, the upper portion of cam 7 is off center with respect to the central axis of opening 35.

Cam 8, on the other hand, has a camming face 36 which is partially circular with respect to the central axis of the opening 35, but this cam also includes a distinct lobe 37 having a diameter greater than that of the rest of the cam. With this arrangement, the single pole, double throw microswitch 12 is in its normally closed relation of throw, so that the gearmotor 2 runs at high speed, when the wheel 15 rides on surface 36 of that portion of cam 8 having the smaller diameter. On the other hand, microswitch 12 is tripped to its normally open relation of throw so that the gearmotor runs at low speed when wheel 15 rides on surface 37 of the lobe of the cam.

With an orientation of lobe 37 in relation to the eccentric upper portion of cam 7 as is shown in FIGS. 4 and 5, clockwise rotation of the cams, as viewed in FIG. 4, results in running of the gearmotor 2 at high speed until rod 18 is driven upward by cam 7 to a point where plate 25 and foot 28 are becoming aproximated so that a crushing force will very soon be brought against a pellet which rests on plate 25. However, just before the pellet is squeezed between the pellet-contacting faces 27 and 29, the wheel 15 on actuator lever 13 of switch 12 rides up onto lobe 37 of cam 8, hence tripping the switch and shifting the gear motor to low speed. Accordingly, the upward thrust of rod 18 proceeds more slowly during compression of the pellet. This provides more reliable testing in that it gives the transducer and related electronic components adequate time to respond to change in the force being applied. However, once the rod 18 has been raised to a maximum elevation by the eccentric of cam 7, a maximum force has been exerted and the pellet has been crushed, so that the gearmotor need no longer run at low speed. Accordingly, wheel 15 of microswitch 12 rides off of lobe 37 of cam 8 and onto surface 36 thereof. This results in the returning of switch 12 to a normally closed relation of throw so that the gearmotor is shifted back to high speed, thereby permitting rod 18 to lower more quickly so that another crushing test can be started.

The thrust assembly, which has already been described with reference to FIGS. 1–3, is shown in larger detail in FIG. 6. A keyway or spline 22 in bushing 19 is represented by the dotted lines and the key 23 which fits therein is thus partially shown by dotted lines as well. It is preferable that rod 18 be non-rotatable in the bushing since the orientation of wheel 24 must be maintained so that it rotatively tracks on the camming surface 34 of cam 7. As shown in the drawings, wheel 24 has an axle 39 which holds it in a yoke at the lower end of rod 18 and the axle is held in place with cotter keys 40. It will be understood, however, that use of a wheel as a cam-riding surface for the rod is not required since the end of the rod could ride directly on the cam, or a ball or a non-rotating low friction bearing surface could be substituted for the wheel. It will also be appreciated that means for adjusting the transducer foot upward or downward in relation to plate 25 can be used in conjunction with means for adjusting plate 25 up or down, or independently thereof.

Figure 7:
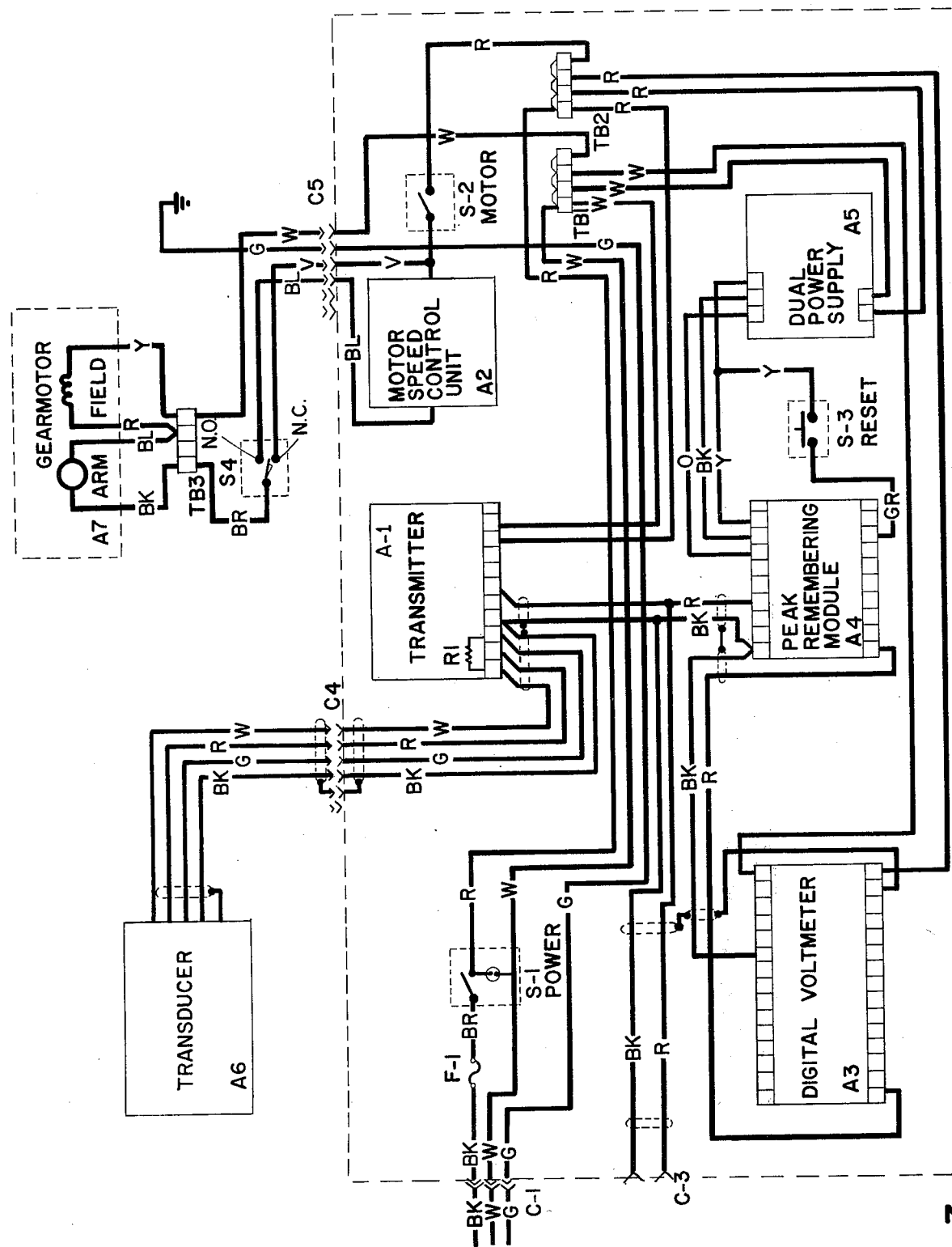
FIG. 7 is a schematic of an electric circuit on interconnected components which can be used with the apparatus shown in FIGS. 1–3.

Referring to FIG. 7, the gearmotor 2 is designated therein as A7, the transducer 17 as A6, and the microswitch 12 as S-4, and will hereinafter be referred to using these letter-figure designations. Excitation current is fed to transducer A6 from transmitter A1 through the black and green lines and current generated by the transducer, upon upward pressing of the foot 28, is fed to the transmitter through the red and white lines. The voltage of the current fed to the transmitter from the transducer is amplified in the transmitter and is thence fed therefrom to a peak voltage remembering module A4 and digital voltmeter A3 through the black and red lines. Operating power for remembering module A4 is supplied thereto through the orange, black and yellow lines from a dual power supply A5. Power at −18 volts is normally fed to the module, but for clearing the memory thereof a nulling current of +18 volts is fed to it by momentarily depressing the normally open reset switch S-3.

Power for the entire system is fed in at connector C1 through the black and white main lines. The green line leading from connector C1 is a common ground. Switch S1 is thus a main switch, and can be a rocker toggle switch with an indicator lamp. Switch S-2, in the red power supply line between terminal block TB2 and motor speed control unit A2, is used to manually turn the gearmotor on or off at the will of the operator.

S-4 is the single pole, double throw microswitch 12 that is actuated by cam 8 to change the speed of the gearmotor. Switch S-4 thus has one fixed pole and two optional poles designated NC and NO. The fixed pole of this switch is connected through the brown-black lead wire to one end of a winding in the motor A7. The NC pole of the switch is attached through the violet lead to one pole of the motor speed control unit A2. The other pole of the speed control unit is connected through the blue lead to the other end of the winding in motor A7. When arranged in this fashion, the motor runs continuously whenever toggle switch S-2 is closed, but the motor speed is changed upon actuation of switch S-4 by means of cam 8. When switch S-4 is in its normally closed relation of throw, the motor receives current at maximum voltage through the violet and white leads from connector C5 and hence runs at full speed. Upon tripping switch S-4 to its normally open relation of throw, motor S-4 receives current through the blue and white leads from connector C5, and hence from the motor speed control unit A2. Therefore, when switch S-4 is actuated to the normally closed or low speed relation of throw, the speed of the motor can be reduced to any selected rmp between full speed and zero revolutions by means of the control unit, and can be set and left at the selected speed at which motor A7 will run each time switch S-4 is thrown to the normally open relation of throw. As was previously indicated, the purpose of adapting the gearmotor to run at two speeds is to permit upward and down movement of thrust rod 18 at maximum speed whenever a pellet is not about to be crushed, whereas the speed at which the thrust rod is moved upward, for crushing of a pellet, becomes much slower whenever the distance between the pellet-contacting faces 27 and 29 of the rod 18 and the transducer foot 28 is such that a pellet is about to be crushed.

Crushing of pellets to determine the crushing strength thereof will now be described with reference to FIGS. 1–7. Switch S-1 is turned on and the unit is allowed to warm up. With the thrust rod 18 in full downward position, so that a space about one-fourth to three-eighths of an inch, for example, exists between the pellet-contacting faces 27 and 29, and with motor switch S-2 in the "stop" relation of throw, a pellet is manually placed on the pellet-contacting face 27 on the top of rod 18. Switch S-2 is then thrown to the "run" position so that motor A7 begins turning at high speed. Thrust rod 18, with the pellet placed on top of it, is thus cammed upward toward the foot 28 of the transducer 30. Just prior to contact of the pellet with face 29 of the foot, switch S-4 is cammed to a normally open relation of throw so that motor A7 and the upward movement of rod 18 are slowed down. When the pellet contacts face 29 of the foot, and as upward movement of rod 18 continues, current is generated by the transducer 17 and is fed to the transmitter A-1. After amplification of this current, it is fed to the digital voltmeter A3 and peak remembering module A4. As compression on the pellet increases, voltage output from transducer increases until the pellet fractures and crumbles, i.e. is crushed, and at which time output voltage from the transducer deminishes greatly even though there may still be some continued upward movement of thrust rod 18. During compression of the pellet, the increase in voltage output can be monitored on voltmeter A3. The purpose of the peak remembering module A4 is to seek and retain the maximum voltage delivered by the transducer and to continue to supply this voltage to voltmeter A3 even after the maximum has been detected, and despite the fact that voltage output from the transducer has fallen to a much lower value or even to zero. The voltage reached at the time the pellet was crushed is thus recorded by the peak remembering module and is displayed by the voltmeter until the module is nulled by pressing the reset switch S-3. Therefore, even though voltage output on crushing of the pellet is recorded only temporarily, sufficient time is thus made available to the operator for ascertaining the maximum voltage and for recording it in a log. As was continuously indicated, thrust rod 18 moves downward after crushing of a pellet, and upon traveling downward to the maximum position permitted by cam 7, motor switch S-2 is manually thrown to stop. The crushed remains of the pellet are then cleaned off the pellet-contacting faces 27 and 29 and a fresh pellet is placed on rod 18 in order to begin another test.

In arriving at a crushing strength value for a batch of pellets, a sample is taken and is screened to obtain pellets of a selected size, e.g. 10, 14, 18 or 35 mesh, the specific size to be tested usually being specified by the buyer of the pelletized material. Advantageously, those pellets which stick within the interstices of the screen are removed therefrom and are retained as the pellets to be tested since they will be more uniform in diameter than pellets which pass through the screen or are retained on it. Thereafter, several of the retained pellets are crushed and the recorded voltages obtained therefrom are averaged. This average voltage is then converted to a crushing strength in terms of grams of force required to crush the pellets. Conversion of voltage to grams of force can be accomplished by means of a table or chart developed by having previously crushed pellets of known crushing strength on the machine to determine which voltages correspond to known crushing strengths expressed in grams.

The instrument is calibrated by applying a known force, in grams, to the foot of the transducer and adjusting a span control of the transmitter to give a desired amplification. For example, the amplification can be set to provide a reading of 0.15 volts for a force of one gram, and the voltmeter reading from crushing of a pellet is then divided by 0.15 to obtain a crushing strength value expressed in grams. Alternatively to use of a table or chart, additional electronic circuitry can be included whereby the value of the voltage generated by the transducer is automatically converted to units of weight during testing of pellets with the machine.

Use of a peak remembering module represents only one manner in which voltage from the transducer, whether converted to weight units or not, can be recorded. Alternatively, the voltage can be fed to a strip chart recorder and charted thereon either as voltage or units of weight. If preferred, either the peak remembering module or the recorder can be dispersed with, but very careful attention of the operator is then required for recognizing and remembering the peak output from the transducer. As shown in FIG. 5, a recorder can be connected to the machine by means of connectors $C_2$ and $C_3$.

Various types of transducers, transmitters, peak remembering modules, voltmeters, power supplies, etc. can be used in the practice of the present invention. One advantageous combination of components is listed below:

A-1, Transmitter — Bell and Howell, Type 18-115 (Resistor R-1 must be selected to null the load cell output and should be a 1% thermally stable resistor)
A-2, Motor Speed Control Unit — Dremel 631003
A-3, Digital Voltmeter — Weston Model 1230
A-4, Peak Remembering Module — Bell and Howell, Type 20-418A-1
A-5, Dual Power Supply — Bell and Howell Type 19-621
A-6, Transducer — Rever Load Cell, UMP Series, 1 lb.

As depicted in the drawings, the transducer 17 is stationarily mounted above the thrust rod 18, and both the thrust shaft 31 and the rod 18 are aligned coaxially and vertically. Alternatively, the transducer can be adapted for movement while using a stationarily mounted force-exerting means. The orientation of the transducer with respect to the force-exerting means is also subject to variation, e.g. the transducer could be located beneath the force-exerting means, or both could be mounted in a horizontal plane whereby one moves laterally in respect to the other. In addition, both the transducer and the force-exerting means could be arranged to move toward each other, and axes along which thrust rod 18 and thrust shaft 31 move can be somewhat misaligned, i.e. other than coaxial. A lever, or the like, can also be substituted for the foot 28 of the load cell.

Thrust rod 18 is shown to be freely slidable and non-rotatable in bushing 19. Alternatively, rod 18 can be connected to primary cam 7, or a suitable eccentric or crank, by means of an interconnecting link pivotally attached to the cam and also the the thrust rod, so that the thrust rod is pulled downward on rotation of the cam rather than being allowed to drift downward by force of gravity. As was previously indicated, the thrust rod can be non-rotatable in the bushing 19, and it will be understood that non-rotation of the rod can be assured by means other than with a key and spline as shown. The rod 18 can, for example, have other than a circular cross-section while using a matching configuration for the opening through the bushing, e.g. a square or hexagonal configuration. Similarly, guide means other than a bushing can be used for rod 18, e.g. stationarily mounted upper and lower brackets with aligned openings therein can be used.

Furthermore, use of a secondary cam 8 for actuating the switch S-4, for changing motor speed, is optional, since the switch could be arranged for actuation by cam 7. It will also be appreciated that another switching means could be included in the electric circuitry of the machine whereby the gearmotor is automatically cut off after each rotational cycle of cam 7, thereby eliminating the need of the operator to actuate switch S-2 to the stop position following the crushing of a pellet. It will also be appreciated that use of a two-speed motor and a motor speed controller are advantageous but optional features.

Therefore, while the invention has been described with reference to specific apparatus, components, combinations thereof, circuitry, sequences of operation, and the like, it will nonetheless be understood that other accordant embodiments will become apparent which are within the spirit and scope of the invention defined in the following claims.

What is claimed is:
1. Apparatus for determining the crushing strength of pellets comprising:
   a. force-measuring transducer which supplies electric current at a voltage which varies in correspondence to a compressive force being exerted on a pellet, said transducer having a foot with a pellet-contacting face thereon which contacts a pellet being crushed,
   b. force-exerting means having a stationarily mounted guide means for a thrust rod that is slidable back and forth within a bushing, said rod having a pellet-contacting face at one end which opposes said face on the foot of said transducer and which contacts a pellet being crushed,
   c. driving means for urging said thrust rod toward the foot of said transducer at a controlled rate until a pellet placed between said pellet-contacting faces is crushed, and d. means for determining the voltage of an electric current supplied by said transducer during the crushing of a pellet.

2. Apparatus as in claim 1 in which said pellet-contacting face is on a pressible foot of said transducer and wherein the axis along which said thrust rod is urged is aligned with the axis along which said foot of the transducer pressed.

3. Apparatus as in claim 1 wherein said faces are approximated but are not in contact with each other during crushing of a pellet, said face on the thrust rod being on a plate that is threadedly attached to the rod, and wherein said plate is threadedly attached to said rod for adjusting the distance between said faces to accomodate the crushing of pellets of different sizes.

4. Apparatus as in claim 1 wherein said bushing has a longitudinally extending spline in the wall thereof and said thrust rod has a key that fits in the spline.

5. Apparatus as in claim 1 wherein the current output from said transducer is fed to a voltmeter having a digital display for the voltage.

6. Apparatus as in claim 5 wherein said current output is first fed to a voltage amplifier before being fed to said voltmeter.

7. Apparatus as in claim 5 and including peak voltage remembering means in combination with said voltmeter whereby the peak voltage fed to the voltmeter during crushing of a pellet is sought, held and displayed by the voltmeter.

8. Apparatus as in claim 7 and further comprising means for clearing said remembering means of a voltage that has already been sought and held.

9. Apparatus as in claim 8 wherein the current output from said transducer is fed to a recording voltmeter.

10. In apparatus for determining the crushing strength of pellets wherein individual pellets are crushed between a force-exerting means and a force-measuring transducer which supplies an electric current at a voltage which varies in correspondence to the force being exerted on a pellet, said transducer having a foot with a face which contacts a pellet being crushed, and further including means for determining said voltage, the improvement wherein said foot of the transducer is located above said force-exerting means and is aligned vertically therewith, said force-exerting means comprising:

a. stationarily mounted guide means for
b. a thrust rod that is slidable back and forth within a bushing, said rod having a pellet-contacting face at one end which opposes said face on the foot of said transducer and which contacts a pellet being crushed, and
c. a driving means for urging the thrust rod toward the foot of said transducer at a controlled rate until a pellet placed between said pellet-contacting faces is crushed.

11. Apparatus as in claim 10 in which said face on the thrust rod is at the upper end of the rod, said driving means includes a rotatable cam, the lower end of said rod contacts said cam, and wherein said rod is urged upward toward said foot upon partial rotation of the cam and then moves downward upon further partial rotation of the cam.

12. Apparatus as in claim 11 wherein said cam is driven by a two-speed electric motor and further including switching means whereby said motor is switched to a lower speed when the faces of said foot and said rod are proximal within an established range and whereby the motor is switched to a higher speed when the distance between said faces is outside of the aforesaid range.

13. Apparatus as in claim 12 and further comprising means for controlling the actual speed of the motor at the lower speed thereof.

14. Apparatus as in claim 12 and further comprising a second cam which actuates said switching means.

15. Apparatus as in claim 11 and including a shaft driven by said motor and wherein both cams are attached to the shaft.

16. Apparatus as in claim 13 wherein said switching means includes a motor speed control unit having two poles and a single pole double throw switch having one fixed pole and two optional poles, and wherein the fixed pole of said switch is connected to one end of a winding of said motor, one of the optional poles of said switch is attached to one pole of said control unit, whereas the other pole of the control unit is connected to a power-supplying line, and wherein the other end of said motor winding is connected to a common line which leads to ground.

17. Apparatus as in claim 11 and further including a freely rotating wheel attached to the lower end of the thrust rod and wherein said wheel contacts said cam and turns during rotation of the cam.

18. Apparatus as in claim 10 wherein said thrust rod is freely slidable in said bushing, said rod being urged upward and toward said foot by said force applying means and being moved downward and away from the foot by gravity after the crushing of a pellet.

19. Apparatus as in claim 18 wherein the axes of said rod and said foot are aligned vertically and coaxially.

20. In apparatus for determining the crushing strength of pellets wherein individual pellets are crushed between a force-exerting means and a force-measuring transducer which supplies an electric current at a voltage which varies in correspondence to the force being exerted on a pellet, said transducer having a face, which contacts a pellet being crushed, and further including means for determining said voltage, the improvement wherein said force-exerting means comprises a thrust assembly having:

a. a stationarily mounted guide means for,
b. a thrust rod that is slidable back and forth within a bushing, said rod having a pellet-contacting face at one end which opposes said face on the foot of said transducer and which contacts a pellet being crushed, and
c. a driving means for urging the thrust rod toward the foot of said transducer at a controlled rate until a pellet placed between said pellet-contacting faces is crushed, and wherein said transducer and the depressible foot thereof are located above said thrust rod, said rod and said foot are aligned vertically and coaxially, said thrust rod is freely slidable in said bushing, said rod being urged upward and toward said foot by said force-applying means and being moved downward and away from the foot by gravity after the crushing of a pellet.

* * * * *

PO-1050
(5/69)

UNITED STATES PATENT OFFICE
CERTIFICATE OF CORRECTION

Patent No. 3,994,157            Dated November 30, 1976

Inventor(s) James R. Burk, Robert C. Bates

It is certified that error appears in the above-identified patent and that said Letters Patent are hereby corrected as shown below:

Column 10, line 13 reads - - Claim 11 - -
             should read - - Claim 14 - -

Signed and Sealed this

Twenty-second Day of February 1977

[SEAL]

Attest:

RUTH C. MASON
*Attesting Officer*

C. MARSHALL DANN
*Commissioner of Patents and Trademarks*